US011510658B2

(12) United States Patent
Speidel et al.

(10) Patent No.: US 11,510,658 B2
(45) Date of Patent: Nov. 29, 2022

(54) SYSTEMS AND METHODS FOR A MULTI-MODALITY PHANTOM HAVING AN INTERCHANGEABLE INSERT

(71) Applicant: Wisconsin Alumni Research Foundation, Madison, WI (US)

(72) Inventors: Michael Antonio Speidel, Madison, WI (US); Lindsay Elizabeth Bodart, Madison, WI (US); Timothy Jon Hall, Madison, WI (US); Amish Naresh Raval, Middleton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 364 days.

(21) Appl. No.: 16/887,939

(22) Filed: May 29, 2020

(65) Prior Publication Data
US 2020/0383663 A1    Dec. 10, 2020

Related U.S. Application Data

(60) Provisional application No. 62/857,754, filed on Jun. 5, 2019.

(51) Int. Cl.
*A61B 8/00* (2006.01)
*A61B 6/00* (2006.01)
(Continued)

(52) U.S. Cl.
CPC .............. *A61B 8/587* (2013.01); *A61B 6/583* (2013.01); *A61B 8/0883* (2013.01); *A61B 8/12* (2013.01);
(Continued)

(58) Field of Classification Search
CPC ....... A61B 8/587; A61B 6/583; A61B 8/0883; A61B 8/12; G06T 7/0012;
(Continued)

(56) References Cited

U.S. PATENT DOCUMENTS 6,318,146 B1 * 11/2001 Madsen ................... A61B 8/08
324/308
9,625,584 B1    4/2017 Cox
(Continued)

OTHER PUBLICATIONS

Bodart, L. E., et al. "Dual-modality phantom for evaluating x-ray/echo registration accuracy." Medical Imaging 2019: Image-Guided Procedures, Robotic Interventions, and Modeling. vol. 10951. International Society for Optics and Photonics, Mar. 2019.
(Continued)

*Primary Examiner* — Siamak Harandi
(74) *Attorney, Agent, or Firm* — Quarles & Brady, LLP

(57) ABSTRACT

A multi-modality phantom is provided. The multi-modality phantom includes a container and an insert. The container defines an exterior that is separated from an interior space and designed to receive a tissue-mimicking medium for an ultrasound imaging process. The container further includes at least one access port formed in the container to perform the ultrasound imaging process of the interior space. The insert can be dimensioned to be selectively arranged within the interior space of the container. The insert includes imaging features arranged to simulate an environment and constructed to yield simultaneous imaging results when performing the ultrasound imaging process and at least one non-ultrasound imaging process.

20 Claims, 8 Drawing Sheets

(51) Int. Cl.
*G09B 23/28* (2006.01)
*A61B 8/08* (2006.01)
*G06T 7/00* (2017.01)
*A61B 8/12* (2006.01)

(52) U.S. Cl.
CPC .......... *G06T 7/0012* (2013.01); *G09B 23/286* (2013.01); *G06T 2207/10116* (2013.01); *G06T 2207/10132* (2013.01); *G06T 2207/30048* (2013.01); *G06T 2207/30056* (2013.01)

(58) Field of Classification Search
CPC . G06T 2207/10116; G06T 2207/10132; G06T 2207/30048; G06T 2207/30056; G09B 23/286; G09B 23/28; G09B 23/285
See application file for complete search history.

(56) References Cited

U.S. PATENT DOCUMENTS

| | | | | |
|---|---|---|---|---|
| 2004/0067591 A1* | 4/2004 | Madsen | ............... | A61B 8/485 600/437 |
| 2005/0123178 A1* | 6/2005 | Teppaz | ............... | G01R 33/58 378/207 |

OTHER PUBLICATIONS

Bodart, L.E., et al., "Clinical feasibility of x-ray based pose estimation of a transthoracic probe using attached fiducials," Proc. SPIE 10576, 1057626 (2018).
Gao, G., et al., "Rapid image registration of three-dimensional transesophageal echocardiography and x-ray fluoroscopy for the guidance of cardiac interventions," IPACI 6135, 124-134 (2010).
Gao, G., et al., "Registration of 3D trans-esophageal echocardiography to Xray fluoroscopy using image-based probe tracking," Med. Image Anal. 16(1), 38-49 (2012).
Hall, T.J., et al., "Ultrasound contrast-detail analysis: A preliminary study in human observer performance," Med. Phys. 20(1), 117-127 (1993).
Hatt, C.R., et al., "A method for measuring the accuracy of multi-modal image fusion system for catheter-based cardiac interventions using a novel motion enabled targeting phantom," Conf. Proc. IEEE Eng. Med. Biol. Soc. 2011, 6260-6264 (2011).
Hosoba, S., et al., "Safety and efficacy of minimalist approach in transfemoral transcatheter aortic valve replacement: Insights from the optimized transcatheter intervention-transcatheter aortic valve implantation (OCEAN-TAVI) registry," Interac. Cardiovasc. Thorac. Surg. 26(3), 420-424 (2018).
Housden, R.J., et al., "Extended-field-of-view three-dimensional transesophageal echocardiography using image-based X-ray probe tracking," Ultrasound Med. Biol. 39(6), 993-1005 (2013).
Hyman, M.C., et al., "Conscious sedation versus general anesthesia for transcatheter aortic valve replacement: Insights from the national cardiovascular data registry society of thoracic surgeons/american college of cardiology transcatheter valve therapy registry," Circulation 136(22), 2132-2140 (2017).
Leon, M.B., et al., "Transcatheter aortic-valve implantation for aortic stenosis in patients who cannot undergo surgery," N. Engl. J. Med. 363(17), 1597-1607 (2010).
Rasche, V., et al., "Fusion of three-dimensional X-ray angiography and three-dimensional echocardiography," Int. J. CARS 2(5), 293-303 (2008).
Reardon, M.J., et al., "Surgical or transcatheter aortic-valve replacement in intermediate-risk patients," N. Engl. J. Med. 376(14), 1321-1331 (2017).
Segars, W.P., et al., "4D XCAT phantom for multimodality imaging research," Med. Phys. 37(9), 4902-4915 (2010).
Wagner, M.G., et al., "Real-time 3D image fusion system for valvular interventions based on echocardiography and biplane x-ray fluoroscopy," Proc. SPIE 10951, 1095173 (2019).
Wagner, M.G., et al., "A dynamic model-based approach to motion and deformation tracking of prosthetic valves from biplane x-ray images," Med. Phys. 45(6), 2583-2594 (2018).

* cited by examiner

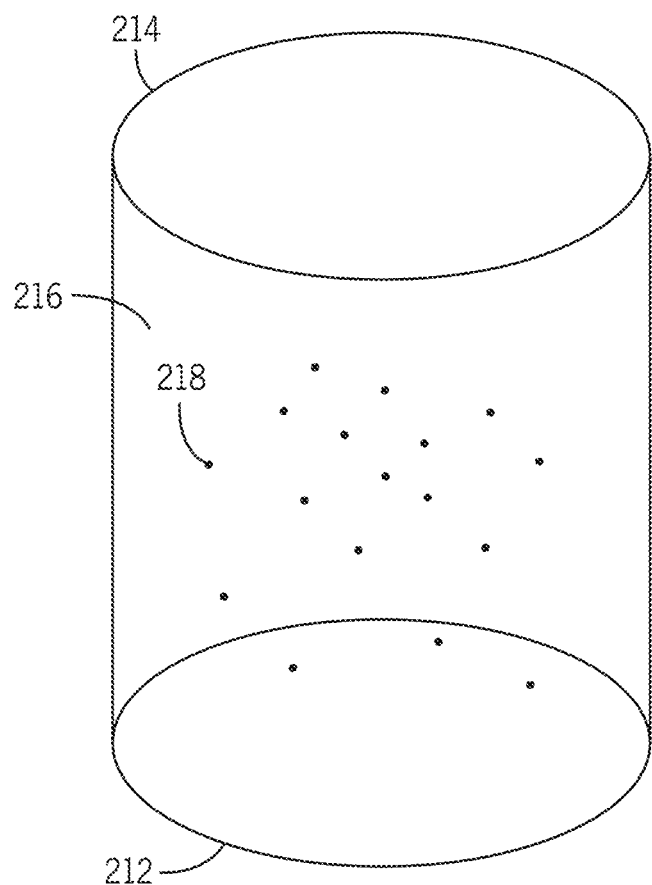
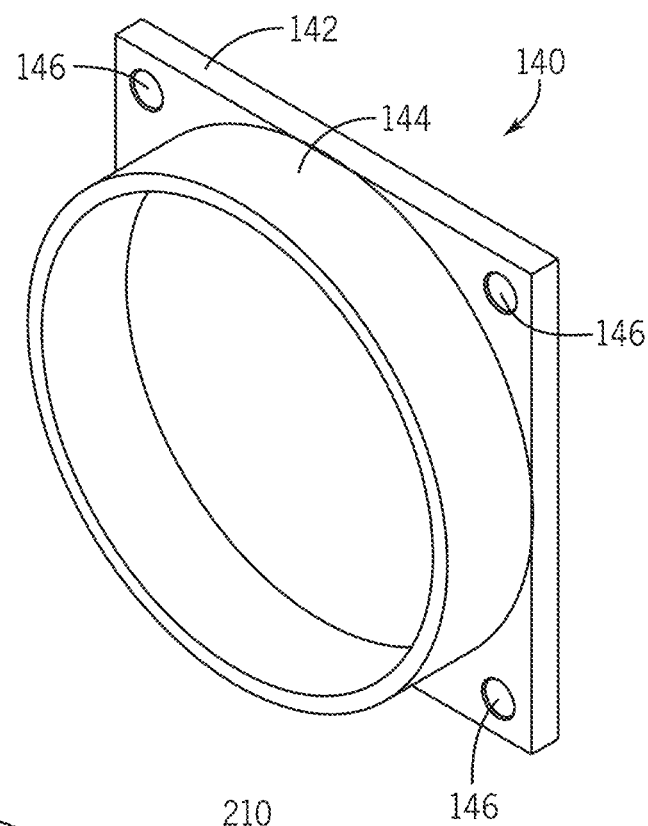
FIG. 7
FIG. 8

SYSTEMS AND METHODS FOR A MULTI-MODALITY PHANTOM HAVING AN INTERCHANGEABLE INSERT

CROSS-REFERENCES TO RELATED APPLICATIONS

This application is based on, claims priority to, and incorporates herein by reference in its entirety U.S. Provisional Application Ser. No. 62/857,754, filed Jun. 5, 2019, and entitled "SYSTEMS AND METHODS FOR A MULTI-MODALITY PHANTOM HAVING AN INTERCHANGEABLE INSERT."

STATEMENT REGARDING FEDERALLY SPONSORED RESEARCH

Not Applicable.

BACKGROUND

Interventional radiology and image-guided interventional procedures are an important part of modern medicine. As just one example, transcatheter interventions for structural heart disease demand real-time visualization of catheter devices and their relationship to cardiac anatomy. In this and many other procedures, device malpositioning due to inadequate visualization can be life threatening and costly. For example, in transcatheter aortic valve replacement, positioning the prosthetic valve too high or too low relative to the aortic valve annulus can cause life-threating paravalvular regurgitation, coronary artery obstruction, or valve embolization.

Therefore, there is a need for systems and methods that facilitate device and soft tissue visualization during interventional procedures.

BRIEF SUMMARY

The present disclosure overcomes the aforementioned drawbacks by providing a multi-modality phantom that can facilitate device and procedure development, improve quality assurance, and/or enable training of clinicians. For example, the multi-modality phantom may include an interchangeable insert that includes a quality assurance environment and/or anatomical simulation structures. The multi-modality phantom may be compatible with a plurality of imaging modalities, which may include x-ray, ultrasound/echocardiography, magnetic resonance imaging, and nuclear imaging, including positron emission tomography and single-photon emission computed tomography.

In one aspect, the present disclosure provides a multi-modality phantom comprising a container and an insert. The container defines an exterior that is separated from an interior space and designed to receive a tissue-mimicking medium for a ultrasound and x-ray imaging processes. The container further includes at least one access port formed in the container to perform the ultrasound imaging process of the interior space. The insert can be dimensioned to be selectively arranged within the interior space of the container. The insert includes imaging features arranged to simulate an environment and constructed to yield simultaneous imaging results when performing the ultrasound imaging process and at least one non-ultrasound imaging process.

In another aspect, the present disclosure provides a multi-modality phantom comprising a container and an insert. The container may include a plurality of echo windows, a first access port, and a drain. The plurality of echo windows may be configured to provide an external ultrasound probe access to a tissue-mimicking medium arranged in the container. The first access port may be dimensioned to receive an interventional device or a transesophageal ultrasound/echocardiography probe. The drain may be configured to add or remove the tissue-mimicking medium from the interior of the container. The insert may be dimensioned to be sealed within the interior of the container and include features configured to be simultaneously visible by x-ray and ultrasound imaging systems.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 7 is an isometric view of a pilot assembly according to aspects of the present disclosure.

FIG. 8 is an insert containing quality assurance markers according to aspects of the present disclosure.

DETAILED DESCRIPTION

Figure 1:
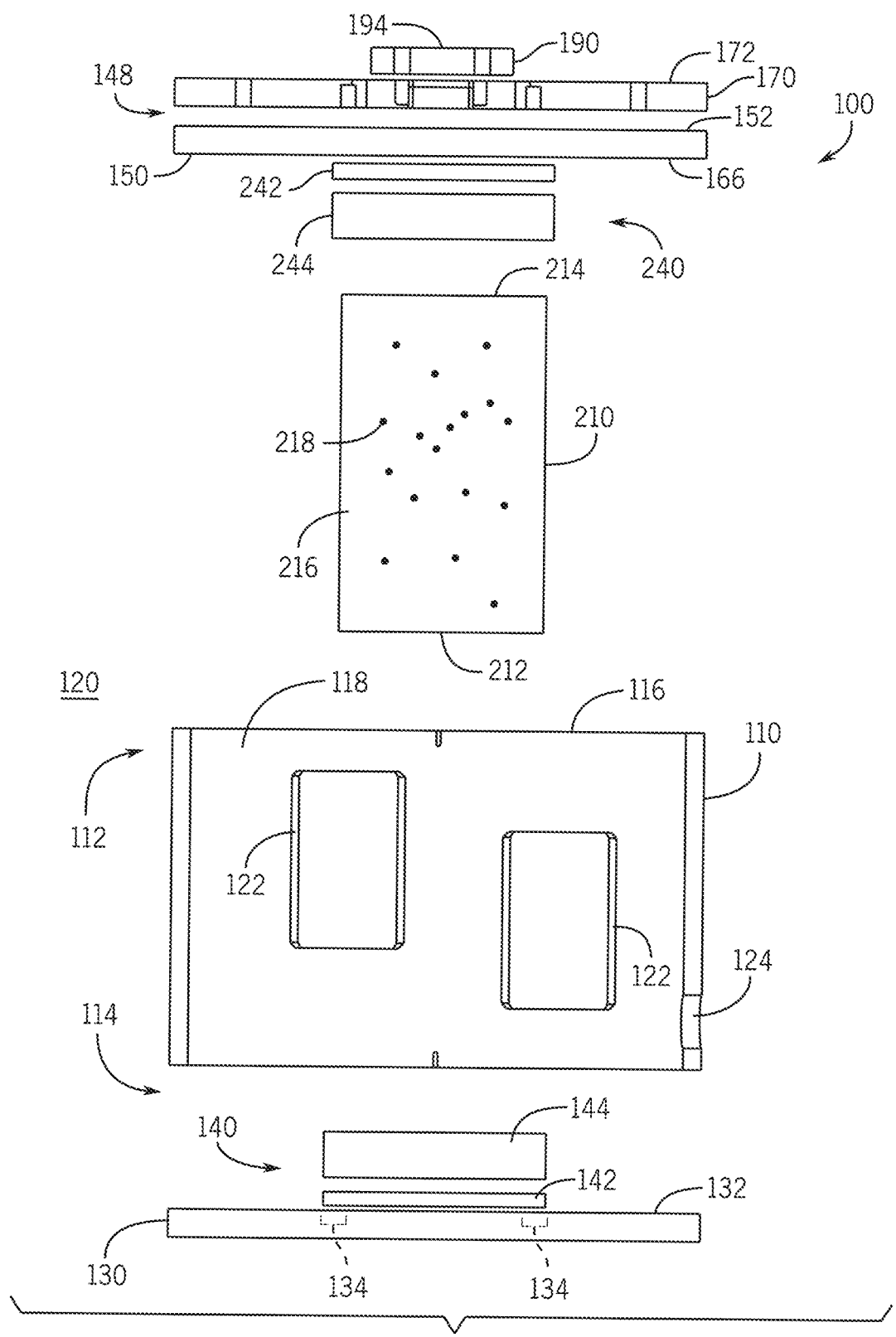
FIG. 1 illustrates one non-limiting example of an exploded front view of a multi-modality phantom according to aspects of the present disclosure.

Before particular aspects of the present disclosure are explained in detail, it is to be understood that the present disclosure is not limited in its application to the details of construction and the arrangement of components set forth in the following description or illustrated in the following drawings. The present disclosure is capable of other configurations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use aspects of the present disclosure. Various modifications to the illustrated configurations will be readily apparent to those skilled in the art, and the generic principles herein can be applied to other configurations and applications without departing from aspects of the present disclosure. Thus, aspects of the present disclosure are not intended to be limited to configurations shown, but are to be accorded the widest scope consistent with the principles and features disclosed herein. The following detailed description is to be read with reference to the figures, in which like elements in different figures have like reference numerals. The figures, which are not necessarily to scale, depict selected configurations and are not intended to limit the scope of the present disclosure. Skilled artisans will recognize the non-limiting examples provided herein have many useful alternatives and fall within the scope of the present disclosure.

Within this specification, embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

FIG. 1 illustrates one non-limiting example of a multi-modality phantom 100 according to the present disclosure. The phantom may include a container 110 and an insert 210. As detailed below, the insert 210 may interchangeable with other inserts in the multi-modality phantom 100 and may be capable of presenting various anatomical and non-anatomical structures to, thereby, simulate a variety of environments suitable for quality assurance, studying and improving device visibility during imaging, providing a clinical training module, facilitating device development, and providing a controlled environment to study the impact of an interventional device on its surroundings. Non-limiting examples of inserts and simulation environments are provided below.

Figure 2:
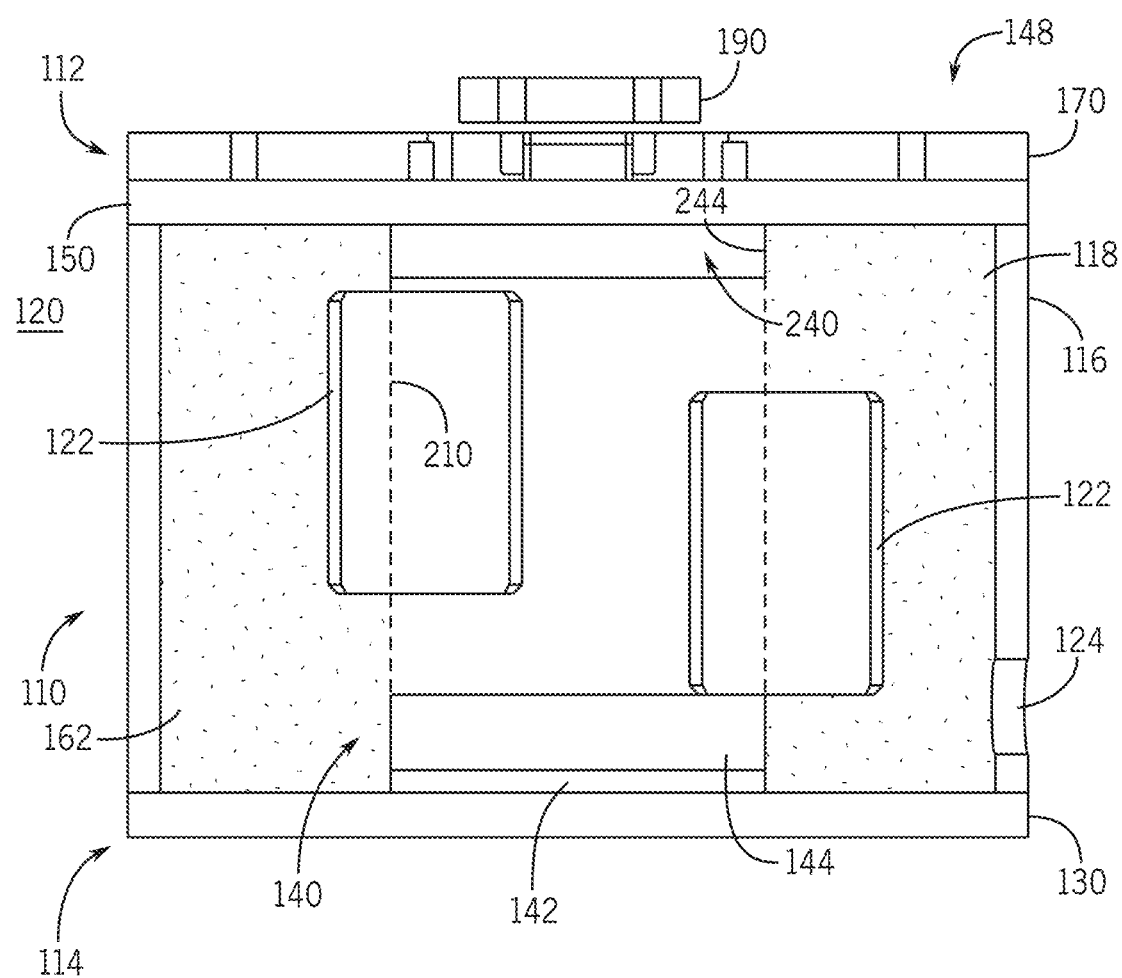
FIG. 2 illustrates one non-limiting example of a front view assembly of a container of a multi-modality phantom according to aspects of the present disclosure.

Referring to FIGS. 1-2, the container may include a top 112, a bottom 114, and a shell 116. The top 112, the bottom 114, and the shell 116 may define an interior space 118 separated from an exterior 120. The shell may include one or more windows 122. The windows 122 may include a plastic lining suitable for ultrasonic imaging to produce views of the interior space 118 from the exterior 120. For example, the windows 122 may be designed to have an ultrasound probe arranged there against to facilitate ultrasound imaging of the interior space 118 from the exterior 120. The windows 122 may also be configured to accommodate alternative imaging modalities. The windows 122 may be arranged in the shell 116 according measurements from a human body to enable realistic simulations. For example, the windows 122 may be arranged in the shell 116 in positions that would be used when performing ultrasound/echocardiography on a human thorax to guide procedures and, correspondingly, the shell 116 may be sized to approximate the human thorax.

The shell 116 of the container 110 may be constructed from a non-metallic material such as plastics, polyvinyl chloride, nylon, and acrylic, for example. The non-metallic material may have properties that do not induce imaging artifacts, such as x-ray image artifacts, MR image artifacts, or the like. The shell 116 may further include an aperture 124. The aperture 124 may serve as a drain port, such that a tissue-mimicking medium, which may be a fluid or have fluid properties, may be readily removed from the phantom. This allows the inserts to be interchanged; the fluid is then returned to the interior using the cavity 160 and 176. Although it's not shown, we attach a spigot/valve to this drain port.

The bottom 114 of the container 110 further includes a bottom plate 130. The bottom plate 130 includes a mounting surface 132 and mounting holes 134, and may be bonded to the shell 116 at the bottom 114 of the container 110, for example, via a solvent cement or other mechanism, such that a hermetic seal may be formed between the bottom plate 130 and the shell 116. The bottom plate 130 may be constructed from a non-metallic material such as plastics, polyvinyl chloride, nylon, and acrylic, for example. The mounting surface 132 and mounting holes 134 may be configured to engage a first pilot assembly 140, as illustrated separately in FIG. 7. The first pilot assembly 140 may include a pilot plate 142, a pilot ring 144, and mounting holes 146 configured to align with the mounting holes 134 of the bottom plate 130. The first pilot assembly 140 may be coupled to the bottom plate 130 using, for example, nylon set screws, pins, rivets or any other suitable coupling mechanism via the mounting holes 134, 146 compatible with a plurality of imaging modalities including x-ray and ultrasound imaging. The second pilot assembly 240 may similarly include a pilot plate 242, a pilot ring 244, and mounting holes.

In another non-limiting example, the first pilot assembly 140 may be integrally formed into the bottom plate 130. In a further non-limiting example, the first pilot assembly 140 may be coupled to the bottom plate 130 via an alternative method such as by adhesive, for example. The first pilot assembly 140 may be configured to receive and secure a first end 212 of the insert 210. The first pilot assembly 140 may facilitate securing the insert 210 such that when the multi-modality phantom 100 is in use, the insert 210 remains stationary relative to the container 110. Similar to the bottom plate 130, the first pilot assembly 140 may be constructed from a non-metallic material such as plastics, polyvinyl chloride, nylon, and acrylic, for example.

Figure 3:
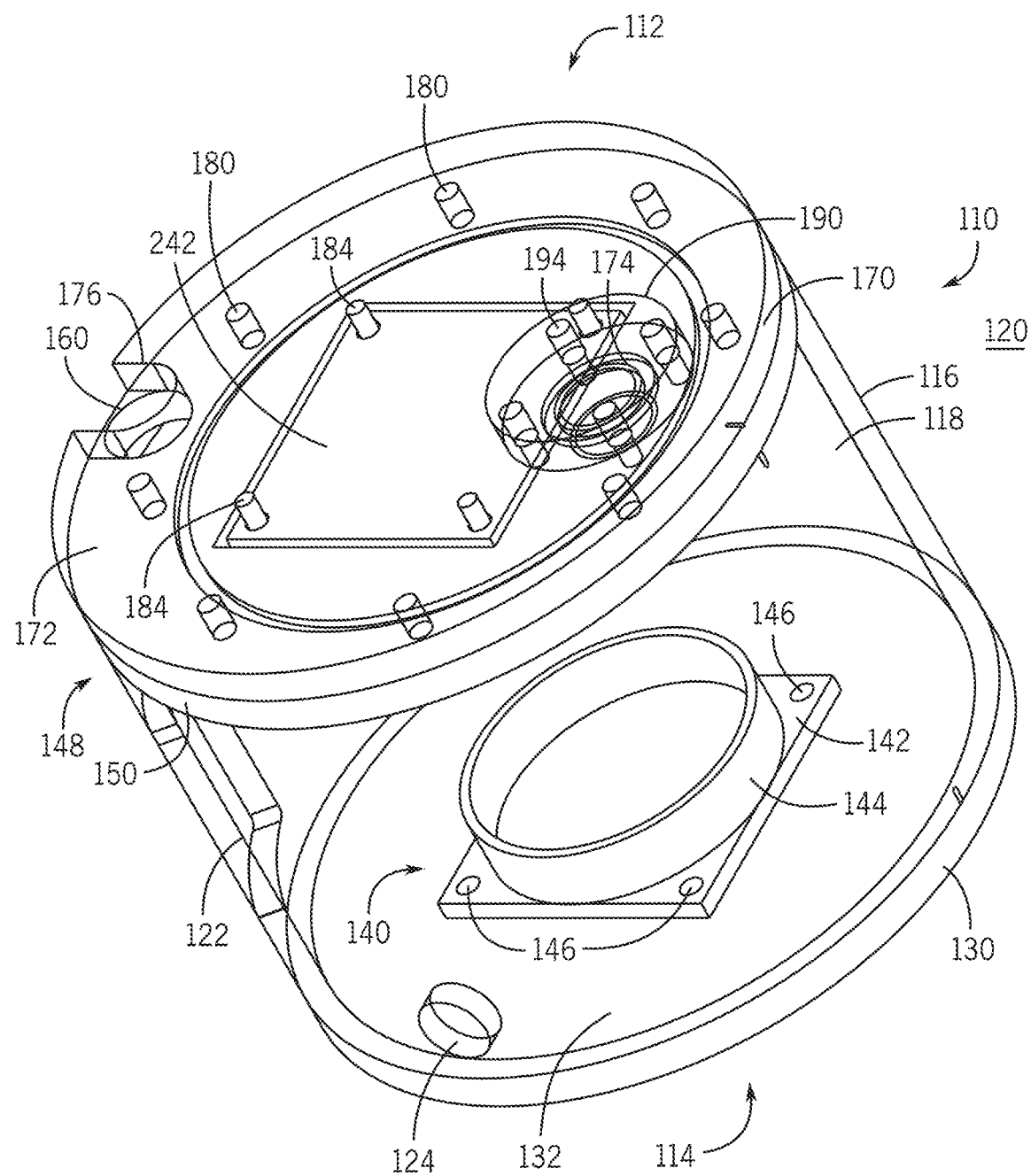
FIG. 3 is a top left isometric view of the container of FIG. 2 according to aspects of the present disclosure.

Further illustrated in FIGS. 1-3, the top 112 of the container 110 may include a top plate assembly 148 comprising a first plate 150, a second plate 170, and a third plate 190. Similar to the bottom plate 130, each of the first plate 150, second plate 170, and third plate 190 of the top plate assembly 148 may be constructed from a non-metallic material such as plastics, polyvinyl chloride, nylon, and acrylic, for example. The top plate assembly 148 may be configured to create a hermetic seal with the shell 116 at the top 112 of the container 110.

Figure 4A:
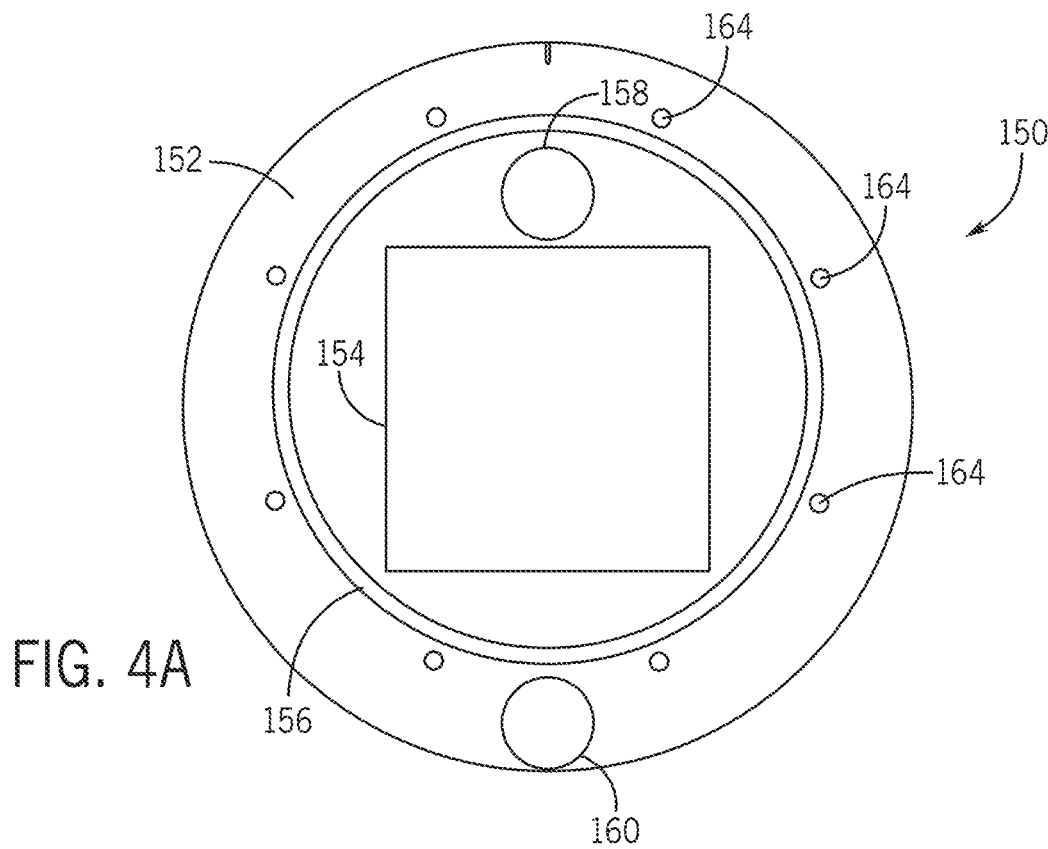
FIG. 4A is a top view of a first plate of a top plate assembly of the container of FIG. 2 according to aspects of the present disclosure.

FIG. 4A illustrates a top surface 152 of the first plate 150. The first plate 150 may include an insert cavity 154, an annular groove 156, a probe cavity 158, and a filling cavity 160. The insert cavity 154 may be dimensioned to allow the insert 210 to pass through the first plate 150 to the interior space 118 from the exterior 120 of the container 110 when the first plate 150 is assembled on the shell 116. The annular groove 156 may be dimensioned to receive a seal, such as an O-ring. The O-ring may provide a seal between the first plate 150 and the second plate 170 when assembled. The probe cavity 158 may be dimensioned to allow an interventional probe, for example, a transoesophageal echocardiography probe (i.e., an ultrasound probe), to pass through. The probe may enter from the exterior 120 to the interior space 118 when the multi-modality phantom 100 is assembled. The filling cavity 160 may extend from the exterior 120 to the interior space 118 such that a tissue-mimicking medium 162 may be added to the interior space 118 of the multi-modality phantom 100 when assembled. The top surface 152 may further include a plurality of mounting holes 164 arranged and dimensioned to receive fasteners to removably couple the second plate 170 to the top surface 152 of the first plate 150.

The tissue-mimicking medium 162 may further facilitate multi-modality imaging. For example, the tissue-mimicking medium 162 may be compatible with ultrasound/echocardiography, x-ray, magnetic resonance imaging (MRI), and nuclear medicine imaging. The tissue-mimicking medium 162 may further have material properties, including tissue-like sound speed, acoustic scattering that provides realistic levels of attenuation, and photon attenuation and scattering comparable to tissue in applicable imaging modalities, for example, x-ray. The tissue-mimicking medium 162 may be a fluid, a gel, or other material.

In one non-limiting example, the following attenuation and speed of sound characteristics may be achieved using a slurry:

| Material | $\alpha = \alpha_0 f^n$ (dB/cm) | $c_s$ (m/s) |
|---|---|---|
| Slurry | $a = 0.27\ f^{1.06}$ | 1526 |

In another non-limiting example, the tissue-mimicking medium 162 may be a distribution of 1-mm diameter agar and graphite particulates suspended in a water-alcohol solution.

Figure 4B:
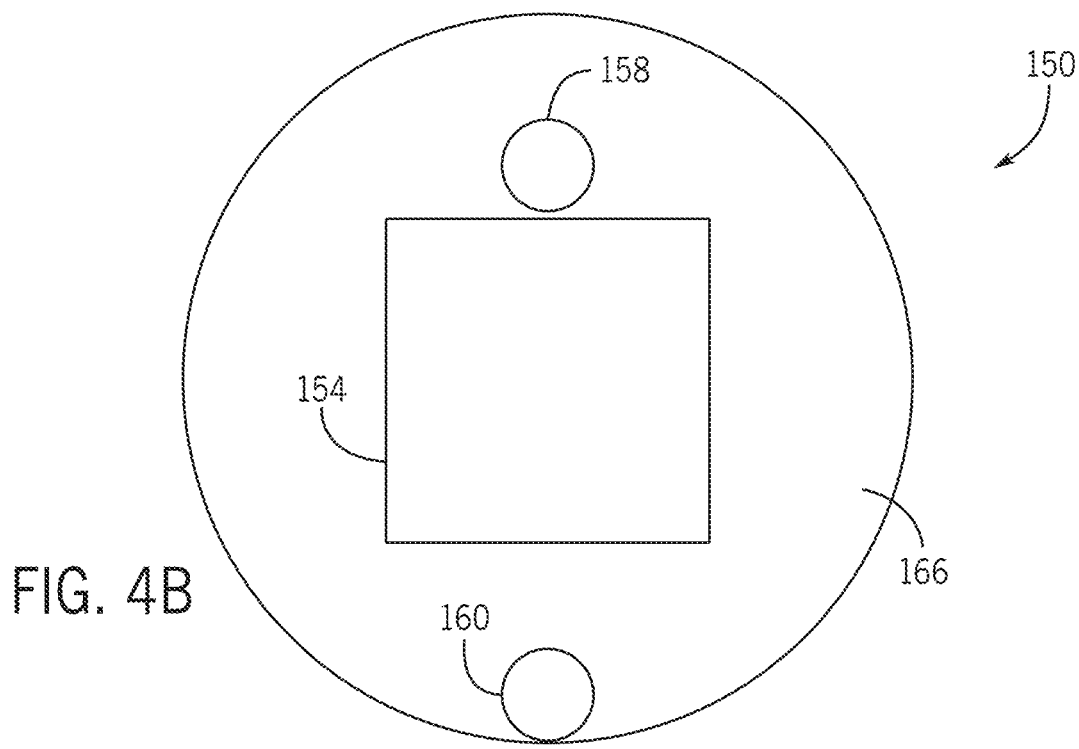
FIG. 4B is a bottom view of the first top plate of the top plate assembly of the container of FIG. 2 according to aspects of the present disclosure.

FIG. 4B illustrates a bottom surface 166 of the first plate 150. Similar to the bottom plate 130, the bottom surface 166 of the first plate 150 may be secured or bonded to the shell 116 at the top 112 of the container 110, for example, via a solvent cement such that a hermetic seal may be formed between the bottom surface 166 of the first plate 150 and the shell 116.

Figure 5:
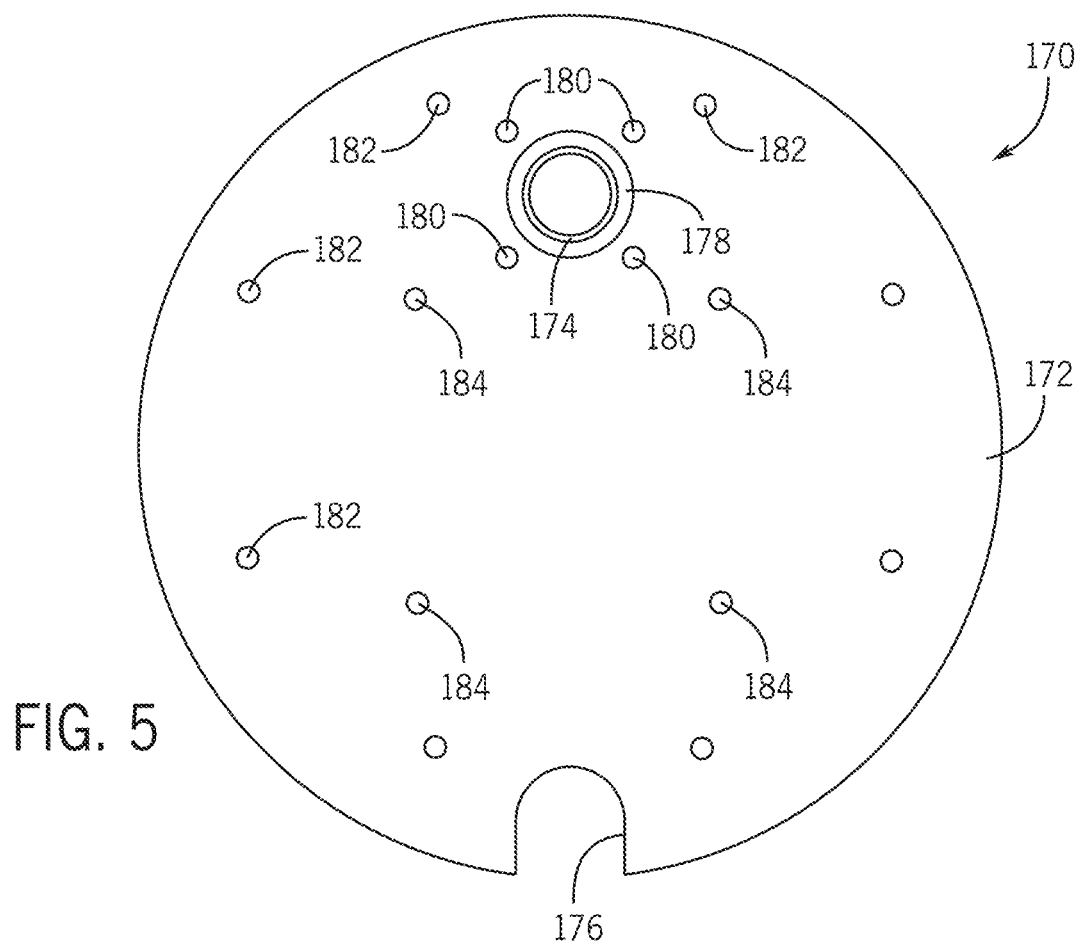
FIG. 5 is a top view of a second top plate of the top plate assembly of the container of FIG. 2 according to aspects of the present disclosure.

FIG. 5 illustrates a top surface 172 of the second plate 170. The second plate further includes a probe cavity 174, a filling notch 176, an annular groove 178, a plurality of mounting holes 180 annularly distributed around the probe cavity 174 for securing the third plate 190, a plurality of mounting holes 182 distributed to align with the mounting holes 164 of the top surface 152 of the first plate 150, and a plurality of mounting holes 184 configured to secure a second pilot assembly 240 to a bottom surface (not shown) of the second plate 170. The second pilot assembly 240 may be configured to receive and secure a second end 214 of the insert 210. The second pilot assembly 240 may facilitate securing the insert 210 such that when the multi-modality phantom 100 is in use, the insert 210 remains stationary relative to the container 110.

The probe cavity 174 may be arranged such that it axially aligns with the probe cavity 158 of the first plate 150 upon assembly of the top plate assembly 148 and may be dimensioned to allow a device, such as a transesophageal ultrasound/echocardiography probe, to pass through. The transesophageal probe may enter from the exterior 120 to the interior space 118 when the multi-modality phantom 100 is assembled. The annular groove 178 may surround the probe cavity 158 and be dimensioned to receive a seal, such as an O-ring. The O-ring may provide a seal between the second plate 170 and the third plate 190 when assembled. The filling notch 176 may be arranged such that it axially aligns with the filling cavity 160 of the first plate 150 upon assembly of the top plate assembly 148 and may be dimensioned such that the tissue-mimicking medium may be added to the interior space 118 of the multi-modality phantom 100 when assembled.

Figure 6:
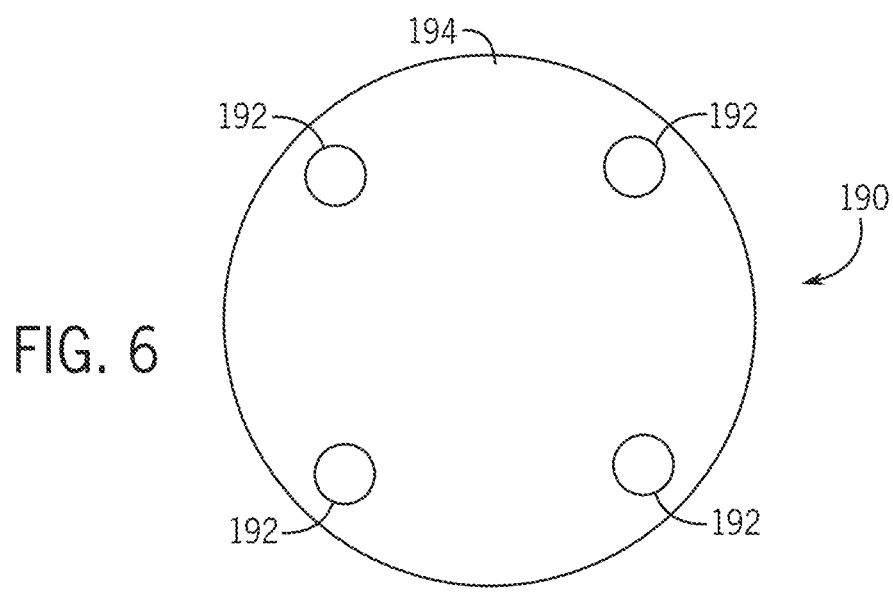
FIG. 6 is a top view of a third top plate of the top plate assembly of the container of FIG. 2 according to aspects of the present disclosure.

FIG. 6 illustrates a top surface 194 of the third plate 190. The third plate 190 further includes a plurality of mounting holes 192 configured to align with the plurality of mounting holes 180 on the second plate 170. The third plate 190 may be removably coupled to the top surface 172 of the second plate 170 using, for example, nylon set screws, pins, rivets or any other suitable coupling mechanism via the plurality of mounting holes 180, 192 compatible with x-ray and ultrasound imaging. The third plate 190 may cover the probe cavity 158, 174 when not in use.

FIG. 8 illustrates one non-limiting example of the insert 210. As mentioned above, the insert may include the first end 212 and the second end 214. The insert may further include a matrix 216. The matrix 216 may be an agar or agar-like substance configured to produce contrasting imaging results of at least two imaging modalities, such as ultrasound/echocardiography, x-ray, MRI, and/or nuclear medicine imaging. The imaging results may be of similar resolution and be of a quality resolution as accepted in medical practice and known in the art. As shown in the present, non-limiting example, the insert 210 may further include one or more quality assurance markers 218 suspended in the matrix 216. In one non-limiting example, the one or more quality assurance makers may be comprised of agar-based spheres incorporating barium sulfate powder and glass microbeads to provide x-ray and ultrasound contrast. The agar-based spheres may be 5 mm in diameter. The glass microbeads may be 53-63 µm in diameter.

Figure 9:
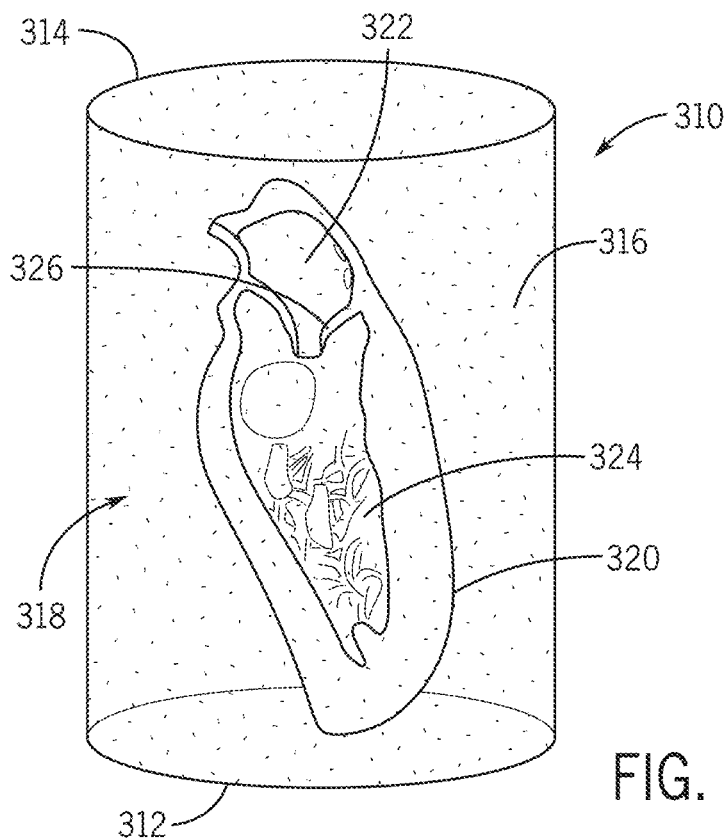
FIG. 9 is an insert formed to resemble an anatomical region, in this case a non-limiting example of a portion of a heart according to aspects of the present disclosure.

FIG. 9 illustrates another non-limiting example of an insert 310. The insert 310 may include a first end 312 and a second end 314. Like the insert 210, the first end 312 may be configured to be secured in the first pilot assembly 140 and the second end 314 may be configured to be secured in the second pilot assembly 240. The insert 310 may further include or form an anatomical structure 318 suspended in or formed as part of a matrix 316. The matrix 316 may be an agar or agar-like substance configured to produce or containing additional materials configured to provide contrast in the resulting images from at least two imaging modalities, such as ultrasound/echocardiography, x-ray, MRI, and/or nuclear medicine imaging. The images may be of similar resolution and be of a quality resolution as accepted in medical practice and known in the art. In one non-limiting example, the anatomical structure 318 may simulate an organ or a portion of an organ. In this non-limiting example, the organ may be a heart 320. The portion of the heart 320 may include a left atrium 322, a left ventricle 324, and a mitral valve 326. In a non-limiting example, the system may be designed to simulate a TAVR valve procedure.

Figure 10:
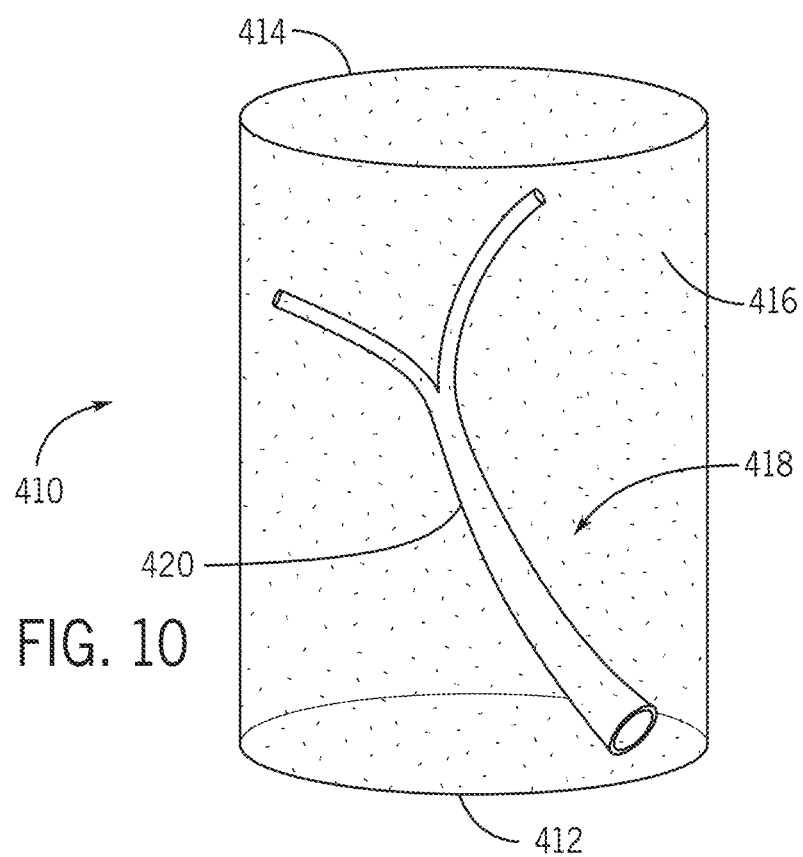
FIG. 10 is an insert formed to resemble an anatomical region, in this case a non-limiting example of a portion of a liver portal vein according to aspects of the present disclosure.

FIG. 10 illustrates another non-limiting example of an insert 410. The insert 410 may include a first end 412 and a second end 414. Like the insert 210, the first end 412 may be configured to be secured in the first pilot assembly 140 and the second end 414 may be configured to be secured in the second pilot assembly 240. The insert 410 may further include an anatomical structure 418 suspended in or formed by a matrix 416. The matrix 416 may be an agar or agar-like substance configured to or containing additional materials that produce contrast in the resulting images from at least two imaging modalities, such as ultrasound/echocardiography, x-ray, MRI, and nuclear medicine imaging. The images may be of similar resolution and be of a quality resolution as accepted in medical practice and known in the art. In one non-limiting example, the anatomical structure 418 may simulate a portion of a portal vein 420 which may be located in a liver.

Figure 11:
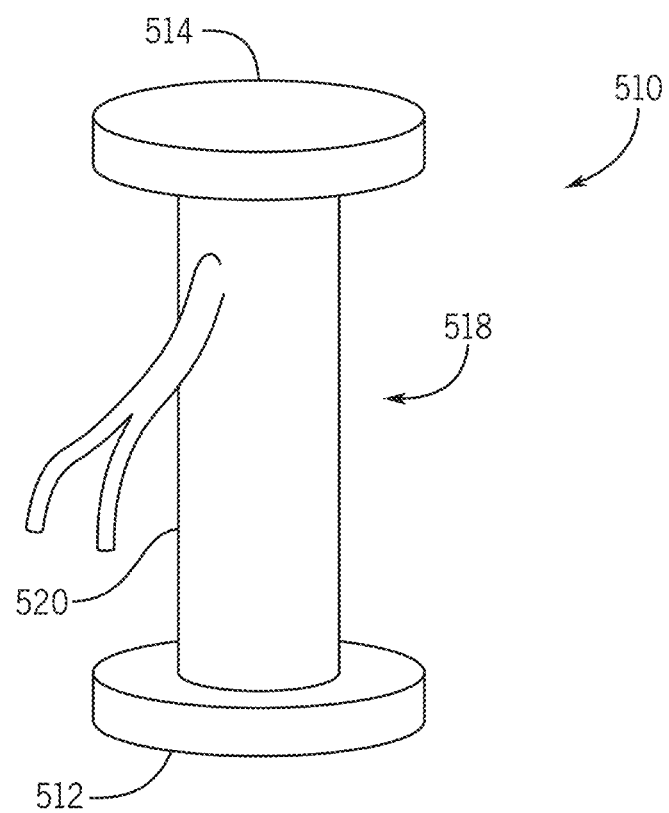
FIG. 11 is an insert formed to resemble an anatomical region, in this case a non-limiting example of a portion of a right hepatic vein according to aspects of the present disclosure.

FIG. 11 illustrates another non-limiting example of an insert 510. The insert 510 may include a first end 512 and a second end 514. Like the insert 210, the first end 512 may be configured to be secured in the first pilot assembly 140 and the second end 514 may be configured to be secured in the second pilot assembly 240. The insert 510 may further include an anatomical structure 518, which may directly interface with the tissue-mimicking matrix or slurry 520. The matrix 520 may be an agar or agar-like substance configured to produce contrast in the resulting images from at least two imaging modalities, such as ultrasound/echocardiography, x-ray, MRI, and/or nuclear medicine imaging. The images may be of similar resolution and be of a quality resolution as accepted in medical practice and known in the art. In one non-limiting example, the anatomical structure 518 may simulate a portion of a hepatic vein 520 which may be located in a liver.

The anatomical structures of FIGS. 9-11 are example configurations of replaceable inserts, and are not limiting. The anatomical structures may be modeled off any organ or vascular structure partially or wholly. Each of the inserts of FIGS. 8-11 may be constructed from a suitable material compatible with a plurality of imaging modalities and may be used for instrumental quality assurance, clinician training, and device development.

While the invention has been described in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

What is claimed is:

1. A multi-modality phantom comprising:
a container defining an exterior separated from an interior space designed to receive a tissue-mimicking medium for an ultrasound imaging process and including at least one access port formed in the container for performing the ultrasound imaging process of the interior space; and
an insert dimensioned to be selectively arranged within the interior space of the container, the insert including imaging features arranged to simulate an environment and constructed to yield simultaneous imaging results when performing the ultrasound imaging process and at least one non-ultrasound imaging process.

2. The multi-modality phantom of claim 1, the container further comprising a cover configured to allow the tissue-mimicking medium and the insert to be arranged in and removed from the interior space of the container and to seal the tissue-mimicking medium and the insert inside the interior space.

3. The multi-modality phantom of claim 2, wherein the at least one access port is integrated in the cover and dimensioned to allow an ultrasound probe to enter the interior space of the container from the exterior.

4. The multi-modality phantom of claim 1, wherein the at least one access port includes at least one window configured to allow the ultrasound imaging process to scan the interior space from the exterior.

5. The multi-modality phantom of claim 1, wherein the tissue-mimicking medium has tissue modeling properties including sound speed, acoustic attenuation and scattering, and x-ray attenuation and scattering.

6. The multi-modality phantom of claim 1, wherein the environment includes at least one of quality assurance markers or anatomical structures.

7. The multi-modality phantom of claim 6, wherein the anatomical structures include vascular or organ structures.

8. The multi-modality phantom of claim 7, wherein the organ structures include at least one of a heart or a liver.

9. The multi-modality phantom of claim 1, wherein the non-ultrasound imaging process is an x-ray imaging process.

10. The multi-modality phantom of claim 1, wherein the container is constructed from an x-ray and ultrasound compatible material and the compatible material includes at least one of a plastic, a polyvinylchloride, a nylon polymer, or an acrylic.

11. The multi-modality phantom of claim 1, wherein the insert is secured in the interior adjacent to a first and second surface of the container.

12. The multi-modality phantom of claim 1, wherein the container includes a first pilot assembly configured to receive and secure a first end of the insert.

13. The multi-modality phantom of claim 1, wherein the container includes a second pilot assembly configured to receive and secure a second end of the insert.

14. A multi-modality phantom comprising:
a container configured to contain a tissue-mimicking medium in an interior space and comprising:
a plurality of acoustic windows configured to provide ultrasound access to the tissue-mimicking medium arranged in the interior space;
a first access port dimensioned to receive an interventional device to extend into the interior space;
a drain configured to remove the tissue-mimicking medium from the interior space; and
an insert dimensioned to be sealed within the interior of the container and comprising features configured to be simultaneously visible by x-ray and ultrasound imaging systems.

15. The multi-modality phantom of claim 14, the container further comprising a top surface configured allow the tissue-mimicking medium to enter the interior space of the container and to seal the tissue-mimicking medium inside the interior space.

16. The multi-modality phantom of claim 14, wherein the features include one of quality assurance markers, an organ structure, and a vascular structure.

17. The multi-modality phantom of claim 16, wherein the organ structures include at least one of a heart or a liver.

18. The multi-modality phantom of claim 14, wherein the tissue-mimicking medium has tissue-mimicking properties including sound speed, acoustic attenuation and scattering, and x-ray attenuation and scattering.

19. The multi-modality phantom of claim 14, wherein the container is constructed from an x-ray and ultrasound compatible material and the compatible material includes at least one of a plastic, a polyvinylchloride, a nylon polymer, or an acrylic.

20. The multi-modality phantom of claim 14, wherein the insert is configured to be secured in the interior space of the container.

* * * * *